Figure 1:
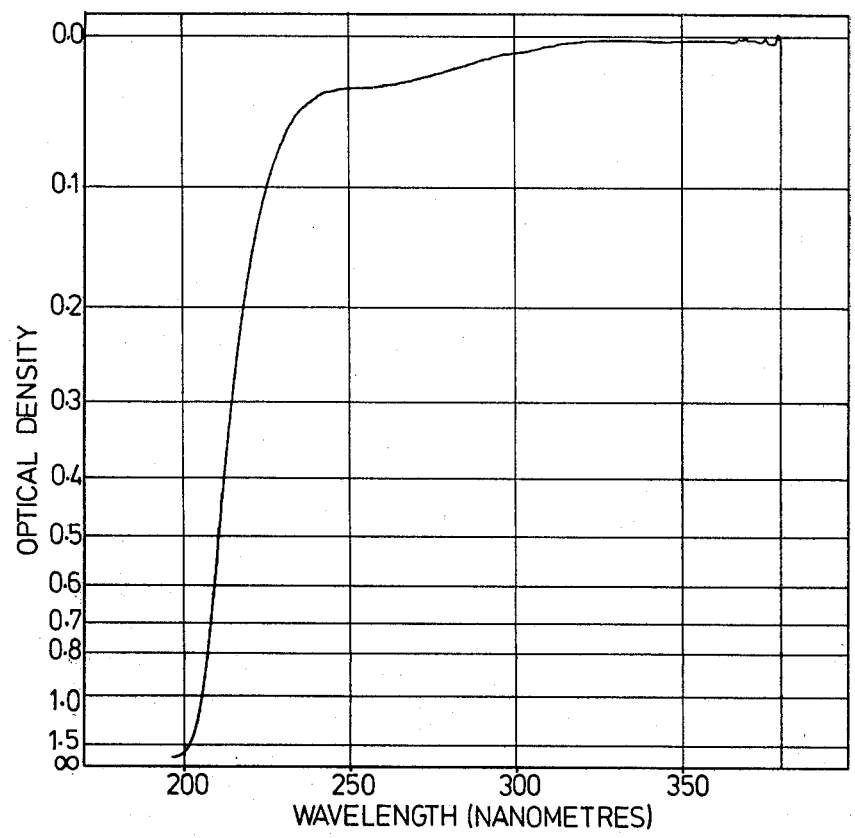

United States Patent [19]

Florent et al.

[11] 4,313,936

[45] Feb. 2, 1982

[54] BIOLOGICALLY ACTIVE SUBSTANCE, ITS PREPARATION AND COMPOSITIONS CONTAINING IT

[75] Inventors: Jean Florent, Boulogne; Jean Lunel, Paris; Denise Mancy, Charenton; Bernard Vuillemin, Yerres, all of France

[73] Assignee: Rhone-Poulenc Industries, Paris, France

[21] Appl. No.: 140,818

[22] Filed: Apr. 16, 1980

[30] Foreign Application Priority Data

Apr. 18, 1979 [FR] France .............................. 79 09743

[51] Int. Cl.³ ...................... A61K 35/00; A61K 35/74
[52] U.S. Cl. .................................... 424/117; 424/92; 435/68; 435/859

[58] Field of Search .................. 424/92, 195, 117; 435/859, 68

[56] References Cited

U.S. PATENT DOCUMENTS 3,821,366 6/1974 Mancy et al. .................... 424/117
4,174,390 11/1979 Hamill et al. .................... 424/117
4,180,564 12/1979 Godfrey et al. .................... 424/117

*Primary Examiner*—Donald B. Moyer
*Attorney, Agent, or Firm*—Stevens, Davis, Miller & Mosher

[57] ABSTRACT

The new water-soluble substance designated by the number 41,200 RP, is obtained from cells of *Micrococcus sedogenes*, M 78 strain (NRRL B-3505), and is particularly useful in human or veterinary therapy for increasing resistance to infections of various origins and for stimulating the natural defences of the organism.

19 Claims, 2 Drawing Figures

BIOLOGICALLY ACTIVE SUBSTANCE, ITS PREPARATION AND COMPOSITIONS CONTAINING IT

DESCRIPTION

This invention relates to a new biologically active substance, hereinafter designated by the number 41,200 RP, which is obtained from cells isolated from a culture of a new microorganism designated by the name *Micrococcus sedogenes* M 78, to a process for its preparation and to pharmaceutical compositions containing it.

The present invention provides the substance designated 41,200 RP which, when isolated from the cells of *Micrococcus sedogenes* M 78 (NRRL B-3505) is an amorphous white, water-soluble powder, containing carbon, hydrogen, oxygen, nitrogen, phosphorus, sulphur, chlorine, sodium and calcium; its elementary composition (calculated for the dry material) is approximately $C=45-47\%$, $H=7.1-7.6\%$, $O=35-38\%$ (by difference), $N=4.0-5.7\%$, $P=0.9-1.2\%$, $Cl=0.1-0.4\%$, S is less than $0.5\%$, $Na=2.0-3.0\%$ and $Ca=0.9-1.9\%$; it comprises (in the anhydrous state) 11 to 18% of aminoacids (of which 5.5 to 7.5% is alanine), 10 to 17% of glucose, 10 to 17% of amino-sugars and less than 5% of nucleic acids; its infra-red spectrum (determined on tablets of a mixture with KBr) shows the principal absorption bands indicated hereinafter in the Table in Example I; and it possesses immunostimulant properties; and alkali metal and alkaline earth metal salts thereof. 41,200 RP is generally isolated with a water content of between 2 and 6%.

The substance 41,200 RP according to the present invention is obtained after treating, with lysozyme, the cells isolated from *Micrococcus sedogenes*, M 78 strain, precipitating the impurities by means of calcium chloride, removing the proteins by treatment with phenol, and then fractionating the product on a molecular sieve.

According to a feature of the present invention there is provided a process for the preparation of the substance 41,200 RP, which comprises:

(a) treating an aqueous suspension of cells of *Micrococcus sedogenes*, M 78 strain (NRRL B-3505), the lysozyme, at a constant pH of from 6.5 to 8, for 1 to 3 hours and at a temperature of the order of 37° C., i.e. of from 30° to 40° C., (b) isolating a crude product, in the form of a salt, from the liquid phase of the resulting suspension and purifying it by progressive precipitation of impurities using calcium chloride in order to obtain the substance 32,919 RP, which may be in the form of an alkali metal or alkaline earth metal salt thereof, and (c) purifying the substance 32,919 RP or salt thereof by treating its aqueous solution with phenol and then fractionating the product on a molecular sieve, the high molecular weight fraction being collected and the substance 41,200 RP being isolated therefrom.

The cells used to prepare the aqueous suspension are preferably dried beforehand and optionally heated at a temperature of the order of 120° C., i.e. of from 110° to 130° C., at a pH of about 3, i.e. of from 2 to 4, for 30 to 60 minutes.

Generally, the lysozyme is used at a rate of 2 to 20 mg per gram of dried cells employed. The treatment with lysozyme is preferably carried out at a constant pH of about 7 preferably for 2 hours, and the treatment is generally effected whilst stirring vigorously.

The liquid phase of the resulting suspension is generally separated off by centrifugation and the dissolved products of low molecular weight are removed either by dialysis across a membrane of suitable porosity or by ultrafiltration. The crude substance thus obtained can be isolated in the form of a salt by lyophilising its solution. At this stage of the preparation, the product obtained consists of proteins, nucleic acids, amino-sugars and less than 5% of polysaccharides and its elementary composition is approximately: $C=41.5-44.9\%$, $H=5.6-5.9\%$, $O=29.4-32.2\%$, $N=11.2-12.6\%$, $P=3.2-4.4\%$, $S=0.1-0.5\%$ and $Cl=0.2-0.4\%$: sulphuric ash content $=11.4-15.4\%$.

Dissolved in water at a concentration of between 10 and 40 grams per liter, preferably 20 grams per liter, the crude substance is generally purified by adding a concentrated solution of calcium chloride until a final concentration of calcium chloride of between 5 and 50 grams per liter, preferably 10 grams per liter, is obtained. The precipitate formed is removed by centrifugation and the resulting solution is dialysed (or ultrafiltered) and then treated with an ion exchange resin carrying a sulphonic acid group in the alkaline form. The substance obtained, which is designated by the number 32,919 RP, can be separated from its aqueous solution by lyophilisation.

The substance 32,919 RP consists of 24 to 33% of aminoacids, 26 to 33% of nucleic acids, 11 to 17.5% of amino-sugars (determination in accordance with the Elson-Morgan method and expression of the results in terms of glucosamine) and 2.8 to 4.3% of polysaccharides and its composition is approximately: $C=44-48\%$, $H=5.2-6.7\%$, $O=29-33\%$, $N=10.0-11.6\%$, $P=2.3-3.7\%$, S is less than $0.5\%$, $Na=3.0-3.8\%$ and $Ca=0.15-0.50\%$.

The substance 32,919 RP is purified again, preferably by the following procedure:

An aqueous solution of the substance 32,919 RP, in which the concentration of the substance 32,919 RP is between 10 and 50 grams per liter, preferably 25 grams per liter, is washed with an equal volume of a phenol/water mixture (preferably containing 10% (w/w) of water) for 15 to 60 minutes, preferably 30 minutes, at a temperature of the order of 65° C. in order to remove the greater part of the proteins. After cooling, the aqueous phase is separated off and washed with a chlorinated hydrocarbon solvent, preferably chloroform, until the dissolved phenol has been removed, and is then dialysed against distilled water. The aqueous phase containing the active substance is lyophilised.

The product thus obtained is dissolved in water buffered to pH 7 using an alkali metal acetate such as sodium acetate. The solution thus obtained is subjected to fractionation on a molecular sieve of high porosity, such as "Ultragel Ac A 22" from the Industrie Biologique Française, or "Sepharose 4 B" or "Sepharose CL 4B" from the Société Pharmacia, the high molecular weight fraction, i.e. from $5 \times 10^5$ to $5 \times 10^6$, being collected. The substance 41,200 RP obtained is then isolated from its solution by lyophilisation, after prolonged dialysis against demineralised water.

The substance 41,200 RP may, if desired, be converted by known methods into an alkali metal or alkaline earth metal salt thereof.

The microorganism *Micrococcus sedogenes*, M 78 strain, of which the culture, under suitable conditions, provides the cells used to prepare 41,200 RP, must be regarded as a new species belonging to the genus Micrococcus.

It was isolated from a sample of soil, taken in Brazil, in accordance with the usual methods for isolating microorganisms. A sample of this strain was deposited at the Northern Regional Research Laboratory of the U.S. Department of Agriculture in Peoria, Ill. (United States), where it was registered on Aug. 14, 1968 under the number NRRL B-3505.

That laboratory is authorised to distribute the strain to any person lawfully having knowledge of the present document.

The characteristics of this microorganism were determined in accordance with the various known identification methods summarised in "Manual of Microbiological Methods", Society of American Bacteriologists, McGraw-Hill Book Company, New York (1957), and also in the following works: J. Dumas, "Bactériologie Médicale" ("Medical Bacteriology"), Editions Médicales Flammarion, Paris (1951); S. Lambin and A. German, "Précis de Microbiologie" ("Monograph on Microbiology"), Collection des Précis de Pharmacie, Masson, Paris (1961); H. Cassagne, "Milieux de culture" ("Culture Media"), Editions de la Tourelle, Paris (1961); and Skerman, "Guide to the Identification of the Genera of Bacteria", The Williams and Wilkins Company, Baltimore (1967).

The Genus was determined in accordance with the identification key in "Bergey's Manual of Determinative Bacteriology", 7th edition, The Williams and Wilkins Company, Baltimore (1957).

The morphological characteristics of the M 78 strain were studied on static cultures kept for 24 hours at 26° C. These cultures consist of immobile, non acid-resistant, Gram-positive coccal cells of diameter 1μ to 1.3μ, which are isolated or in groups of two or four cells, or in short chains of 4 to 16 cells, or also in non-uniform agmina of 20 to 50 cells. The presence of spores was not observed.

The cultures on nutrient agar slopes have the appearance of a smooth or very slightly rough, odourless, non-chromogenous, abundant greasy coating having a soft consistency. The cultures on nutrient agar in Petri dishes are in the form of circular colonies with uniform edges and a smooth surface; these colonies are flattened or slightly convex and more or less opaque.

The cultures in nutrient glucose broth are moderately turbid, do not contain pigment, are odourless and contain a flake-like sediment.

When cultivated on potato, the M 78 strain forms a very pale yellowish-white, smooth greasy coating which does not blacken the potato and does not contain soluble pigment.

The biochemical characteristics were studied on cultures incubated at 26° C., and are summarised as follows:
Respiratory type: obligate aerobe
Reduction of nitrates to nitrites: positive
Chromogenesis: negative
Indole production: negative
H$_2$S production: negative
Gelatin liquefaction: negative over 21 days
Casein hydrolysis: positive
Methyl red test: negative
Test for the production of acetyl-methyl-carbinol (Voges-Proskauer reaction): negative
Cultivation on skimmed milk: no coagulation, no peptonisation, alkalinisation of the medium from pH 6.1 to pH 7.5 between the 1st and the 21st day
Optimum temperature for development: 4° C.—no development; 22° C.—good developement; 26° C.—very good development; 30° C.—good development; 37° C.—mediocre development; 45° C.—no development
Catalase: positive
Oxidase: negative
Formation of acids from the following carbohydrates and polyhydric alcohols (in aerobiosis and anaerobiosis), as detected by a colour change in phenol red:
glucose: negative
galactose: negative
arabinose: negative
sucrose: negative
lactose: negative
mannitol: negative
glycerol: negative
Starch hydrolysis: positive
Esculin medium: no blackening
Cultivation on a medium containing high concentrations of added NaCl:
4% of NaCl: average development
10% of NaCl: no development
Use of urea as the only source of nitrogen: negative
Urease: negative
Chitin hydrolysis: negative
Cultivation on a medium for autotrophs [with $(NH_4)_2SO_4$ as the only source of nitrogen]: no development; no formation of nitrites from $NH_4^+$.

Following the principle of Pridham's method [Journal of Bacteriology, 56, 107–114 (1948)], the M 78 strain utilises the following substances, with a moderate or good degree of efficiency, as sources of carbon: starch, ethanol, sodium acetate, sodium propionate, succinic acid, malic acid, sodium citrate and sodium pyruvate. The following are not utilised or only permit poor development: ribose, arabinose, glucose, lactose, maltose, sucrose, trehalose, glycerol, mannitol, inositol, glutaric acid, sodium tartrate and galacturonic acid.

The sources of nitrogen which can be utilised by the M 78 strain for its development were also determined in accordance with Pridham's method, using sodium citrate as the source of carbon and replacing the $NH_4H_2PO_4$ in the base medium by various nitrogen-containing compounds. Under these conditions, the following compounds are utilised with a good or moderate degree of efficiency: $NaNO_3$, $NaNO_2$, $NH_4H_2PO_4$, D,L-asparagine, succinimide, glycine, D,L-alanine, D,L-aspartic acid, D,L(+)-glutamic acid, L(−)-tyrosine and D,L-proline. the following are not utilised: adenine, uracil, creatinin, D(+)-glucosamine, sarcosine, L(+)-arginine, D,L-methionine and betaine.

With reference to the identification key in "Bergey's Manual of Determinative Bacteriology", 7th edition, The Williams and Wilkins Company, Baltimore, 1957, the fact that the bacterial cells studied do not contain photosynthetic pigments, that they are incapable of developing on a medium for autotrophs, that they reproduce by scissiparity, that they are spherical and are isolated, in short chains or in non-uniform agmina, and that they do not possess trichomas, makes it possible to classify the M 78 strain in the order of the Eubacteriales (Buchanan, 1917).

On the other hand, the bacterium M 78 is spherical, Gram-positive and an obligate aerobe, reduces nitrates to nitrites, is incapable of fermenting carbohydrates in anaerobiosis and does not form spores; these characteristics make it possible to classify it in the family of the Micrococcaceae (Pribram, 1929).

This family is divided into six genera which are split into two groups in accordance with the respiratory type; this distinction makes it possible to classify the bacterium M 78 in the first group, which comprises the genera Micrococcus, Staphylococcus, Gaffkya and Sarcina. This group is split into two sub-groups which are characterised by the manner in which the cells are grouped together. The bacterial cells studied do not occur systematically in tetrads or in groups of eight cells; as a result of this property, the M 78 strain is classified either in the genus Micrococcus or in the genus Staphylococcus.

A large number of characteristics, in particular the fact that the M 78 strain is incapable of fermenting glucose in anaerobiosis and that it is an obligate aerobe, makes it possible to relate it to the genus Micrococcus.

In order to determine the genus more precisely, comparisons were made, for numerous tests, with *Staphylococcus aureus* 209 P, *Neisseria catarrhalis* A 152 (IP), *Streptococcus faecalis* ATCC 8043 and *Streptococcus faecalis* ATCC 9790, and this made it possible to eliminate these various genera having coccal cells, some of which genera belong to families other than the Micrococcaceae Amongst the 16 described species belonging to the genus Micrococcus, those which the M 78 strain could most closely resemble are as follows: *Micrococcus varians, Micrococcus caseolyticus* and *Micrococcus colpogenes.*

The M 78 strain differs, in particular, from *Micrococcus varians* in that it does not form acids from glucose, lactose, sucrose, glycerol or mannitol and in that it does not acidify milk.

It differs from *Micrococcus caseolyticus* in that it does not liquefy gelatin, does not peptonise milk and does not produce acids from glucose, lactose, mannitol or glycerol.

The M 78 strain is also different from *Micrococcus colpogenes* by the essential fact that it cannot hydrolyse chitin and that it is also urease-negative.

In short, the strain studied exhibits differences, from the described species of the genus Micrococcus, which make it possible to consider it as a new species.

The process for the preparation of the cells used to prepare 41,200 RP consists in cultivating *Micrococcus sedogenes,* M 78 strain, on a suitable medium and under suitable conditions, and then in separating off the cells which have multiplied during cultivation.

*Micrococcus sedogenes,* M 78 strain, can be cultivated by any surface or submersion method of aerobic cultivation, but the latter method is preferable for reasons of convenience. The inoculation and fermentation techniques and the various types of equipment used for this purpose are those commonly used in the fermentation industry.

The fermentation medium must contain sources of assimilable carbon, nitrogen, phosphorus and sulphur, inorganic substances and, if appropriate, growth factors. These constituents may be provided in the form of well-defined products or by complex mixtures such as those encountered in biological products of various origins.

Sources of assimilable carbon which can be used are carbohydrates, such as dextrins and starch, or other carbon-containing substances, such as alcohols (ethanol) or certain organic acids, e.g. lactic acid and citric acid. Certain animal or vegetable oils, such as lard oil or soya bean oil, can advantageously replace these various sources of carbon or can be added thereto.

Suitable sources of assimilable nitrogen are extremely varied. They may be very simple chemical substances, such as inorganic or organic ammonium salts and certain aminoacids. They can also be provided by complex substances which mainly contain nitrogen in protein form, e.g. casein, lactalbumin, gluten and their hydrolysates, soya bean flour, peanut flour and fish meal, meat extract and yeast extract, soluble residues from the distillation of gran alcohol (distillers' solubles), and cornsteep liquor.

The sulphur and the phosphorus are generally provided in a sufficient amount by the complex substances mentioned above. They can also be provided in the form of sulphates and phosphates.

Some of the inorganic constituents added can have a buffering or neutralising effect, such as alkali metal or alkaline earth metal phosphates or calcium carbonate or magnesium carbonate. Others contribute to the ionic equilibrium necessary for the development of *Micrococcus sedogenes,* M 78 strain, such as alkali metal and alkaline earth metal chlorides and sulphates or salts of zinc, cobalt, iron, copper and manganese.

The pH of the fermentation medium at the start of cultivation must be between 6.0 and 7.8 and preferably between 6.5 and 7.5. The optimum temperature for the fermentation is between 25° and 30° C. but satisfactory production is achieved at temperatures between 20° and 35° C.

The aeration of the fermentation can vary between fairly wide limits. However, it has been found that aerations of 0.3 to 3 liters of air per liter of medium per minute are particularly suitable. The maximum yield is obtained after 8 to 20 hours of cultivation, preferably after 15 hours, the time depending on the medium used.

The pH of the fermentation medium at the end of cultivation is generally between 7.3 and 8.8 and it is preferably between 8.0 and 8.4.

The microorganism *Micrococcus sedogenes,* M 78 strain, is generally separated from the fermentation medium by filtration or centrifugation, advantageously after the medium has been acidified to a pH of about 3 by adding a mineral acid, such as hydrochloric acid. For the subsequent treatments, it is possible either to use the crude cells thus obtained, or to dehydrate them by lyophilisation or by washing with alcohol or with acetone, and then to dry them under reduced pressure in order to obtain purified dry cells. It can be particularly advantageous to heat the resulting cells at a temperature between 120° and 130° C., for 30 to 60 minutes, before their subsequent use.

The new substance 41,200 RP according to the present invention exhibits remarkable and useful biological properties.

When administered to mice intravenously, subcutaneously, intraperitoneally or intranasally, the substance according to the invention significantly increases the resistance of the mice to infection by doses, which are normally fatal, of virulent strains of bacteria, such as *Listeria monocytogenes, Staphylococcus aureus* and *Escherichia coli,* and of viruses, such as encephalomyocarditis virus, murine hepatitis virus, influenza viruses (human viruses adapted to mice, type $A_0$ and $A_2$), herpes virus and Semliki-Forest arbo-virus. The condition of increased resistance persists for at least 96 hours after the treatment.

When administered to mice parenterally, 41,200 RP strongly stimulates the phagocytic ability of the reticulo-endothelial system and increases the number of antibody-producing lymphocytes in the spleen. It exerts a stimulating effect on reactions involving delayed-type hypersensitivity and reactions involving the production of antibodies against particulate antigens.

In mice in which tumoral cells (such as sarcoma 180 cells) have been grafted, 41,200 RP favours rejection of the tumors by causing a necrotic reaction therein.

Under certain conditions, the product according to the invention increases the number and/or the cytolytic activity of the T lymphocytes in the spleen, against allogenic tumoral cells.

In animals (mice), depending on the experimental systems used and the methods of administration, the active doses are generally between 0.03 and 3 mg/kg animal body weight, and preferably between 0.3 and 1 mg/kg animal body weight. Generally, a single treatment suffices to achieve the desired effect for a period of at least 48 hours.

In mice, the 50% lethal dose ($LD_{50}$) of 41,200 RP, administered intravenously, is of the order of 23 mg/kg animal body weight.

In the following text: proteins are expressed according to the aminoacid analysis, glucose is determined by the anthrone method, phosphorus is determined by the molybdate method after ashing, the proportion of nucleic acids is determined by the absorbency at 258 nm, and amino-sugars are determined by the Elson-Morgan method and are expressed in terms of glucosamine, or by determination with ninhydrin, after hydrolysis and separation using a Biotronik LC 6000 E autoanalyser.

By the expression "known methods" as used in this Specification and the accompanying claims is meant methods heretofore used or described in the chemical literature.

The following Examples illustrate the present invention

EXAMPLE 1

(A) Preparation of the cells

Peptone (1,200 g), meat extract (600 g), soya bean oil (1,200 cc) and tap water (sufficient to make up to 110 liters) are introduced into a 170 liter fermenter.

The pH is adjusted to 6.90 by adding 10 N sodium hydroxide solution and the medium is then sterilised by bubbling steam at 122° C. through it for 40 minutes. After cooling, the volume of the broth is 120 liters because steam has condensed during the sterilisation; the pH of the medium is 6.70. Inoculation is carried out with a culture, produced in a stirred Erlenmeyer flask, of *Micrococcus sedogenes*, M 78 strain (200 cc).

The culture is developed at 27° C. for 14 hours, whilst stirring and aerating with sterile air; it is then suitable for inoculating the production culture.

The production culture is carried out in an 800 liter fermenter containing the following: L-lactic acid (4 kg), soya bean oil (2 liters), ammonium sulphate (2.4 kg), sodium chloride (2 kg), monopotassium phosphate (0.4 kg) magnesium sulphate. $7H_2O$ (0.8 kg), copper sulphate. $5H_2O$ (0.02 kg), zinc sulphate. $7H_2O$ (0.012 kg), cobalt chloride. $6H_2O$ (0.008 kg) and tap water (sufficient to make up to 370 liters).

The pH of the medium is adjusted to 7.10 by adding 10 N sodium hydroxide solution (2,950 cc) and the broth is then sterilised by bubbling steam at 122° C. through it for 40 minutes. After cooling, the volume of the broth is 400 liters because steam has condensed during the sterilisaton; the pH of the broth, which is 4.20, is adjusted to 6.60 by adding a 5 N aqueous solution of sodium hydroxide (2,100 cc).

Inoculation is then carried out with 40 liters of the inoculum culture described above, produced in the 170 liter fermenter. The culture is developed at 27° C. for 16 hours, whilst stirring with a stirrer rotating at 205 rpm and aeration with sterile air (15 $m^3$/hour).

At the end of the operation, the pH of the culture medium is 8.20 and the volume of the broth is 440 liters. The must thus obtained is cooled to +4° C. and its pH is adjusted to 3 by adding 5 N hydrochloric acid (4 liters). The cells are isolated by centrifugation at 4,000 rpm (2,900 g). The cells are taken up in ethanol (80 liters) at −10° C., by stirring for 15 minutes, and are then isolated by centrifugation and dried at 35° C. under reduced pressure (5 mm Hg) for 15 hours. Dry cells (1,500 g) are thus obtained.

(B) Preparation of 32,919 RP

Cells (1 kg) prepared as described in (A) are suspended in sterile distilled water (40 liters), in a stainless steel reactor which is equipped with a jacket, the temperature of which is thermostatically controlled by the circulation of water, and with a high-powdered central stirrer. The pH is adjusted to 7.0 by adding 10 N sodium hydroxide solution.

Lysozyme (2 g) is then added and the mixture is stirred for 2 hours at 37° C., the pH being periodically readjusted to 7.0 by adding 5 N sodium hydroxide solution.

The mixture is then centrifuged on a Sharples M16 machine (2 successive passes at 17,000 rpm with a flow rate of 30 liters per hour). The supernatant (37 liters) is ultrafiltered (UFP 20 apparatus equipped with an Iris 3042 acrylic membrane), the retained material being recycled and demineralised water (3×40 liters), cooled to +4° C., being added.

Concentrated retained material (7 liters), which has been freed of its small molecules (molecular weight below about 25,000 daltons), is thus collected. Its pH is readjusted to 7 with 5 N sodium hydroxide solution, and the resulting solution is then lyophilised. Crude product (147 g) is thus obtained.

This product (31 g) is dissolved in demineralised water (1,550 cc), at a temperature of about 20° C., by stirring for 30 minutes; an aqueous solution containing 668 g/liter of calcium chloride dihydrate (31 cc) is then added in the course of 5 minutes, whilst stirring constantly; stirring is continued for 30 minutes. The precipitate formed is removed by centrifugation on a Sharples laboratory machine at 40,000 rpm with a flow rate of 5 liters per hour. The supernatant is dialysed on a cellulosic membrane for 3 days, at +4° C., against demineralised water (3×40 liters).

The retained material is then treated for 1 hour, in a round-bottomed flask, with Dowex 50 X2 polystyrenesulphonic resin in the sodium form (310 cc), whilst stirring; the resin is filtered off and washed on the filter with water (310 cc). The wash waters are combined with the filtrate and the whole is lyophilised.

32.919 RP (17 g) is thus obtained in the form of a salt having the following characteristics:
appearance: white powder;
composition: water (Fischer)=15.7%, referring to the dry material: proteins (sum of the aminoacids)=24.6%,
polysaccharides=3.9%,
nucleic acids=28.9% (according to the UV spectrum).
elementary analysis: C=46.30%, H=5.84%, O (by difference)=30.71%, N=10.04%, P=3.11%, S is less than 0.5%, Na=3.70% and Ca=0.30%.

(C) Purification of the 32,919 RP

The substance 32,919 RP obtained under the conditions of Example (B) (25 g) is dissolved in demineralised water (1 liter) contained in a 2 liter reactor which is equipped with a stirrer and a temperature-regulating device; a phenol/water mixture (109 cc of water to 1 kg of phenol) (1 liter) is added. The mixture is heated to 65° C., whilst stirring vigorously. Stirring is continued for 30 minutes at the same temperature. After rapidly cooling the reactor to a temperature of about 25° C. by means of an ice bath, the phases are separated by centrifugation at 3,300 g, for 30 minutes, on a cooled laboratory machine (Jouan, type K 63 F, with a capacity of 4 liters). 450 cc of aqueous phase are thus obtained.

The phenol phase and the intermediate phase are re-extracted with demineralised water (1 liter) for 30 minutes at 65° C; after cooling and centifugation, as indicated above, a further 1,470 cc of aqueous phase are obtained. The aqueous phases are combined. The phenol is removed by successive washings with chloroform (2×2 liters). The aqueous phases are then clarified by centrifugation for 30 minutes at 3,300 g. 1,800 cc of aqueous phase are thus obtained. This clarified aqueous phase is then dialysed for 3 days, at +4° C., against demineralised water (3×40 liters). The retained material is lyophilised and a white amorphous powder (14.5 g) is thus obtained.

This powder (8 g) is dissolved in a sterile 0.1 M sodium acetate buffer at pH 7 (400 cc) [analytical-grade sodium acetate (136.09 g) is dissolved in demineralised water (0.9 liter), the pH is then adjusted to 7.0 by adding acetic acid (d=1.049) and the volume is made up to 1 liter; sterilisation is carried out by heating for 45 minutes at 122° C.; this solution is diluted in a ratio of 1/10 with sterile demineralised water at the time of use].

The resulting solution is poured onto a Sepharose CL 4B column (diameter: 13.5 cm, height: 65 cm) which is installed in a cold chamber (+4° C.) and treated with sterile 0.1 M sodium acetate buffer at pH 7.0. Elution is then carried out with the same buffer at a rate of 1.33 liters/hour and the absorbency at 230 nm, through 0.1 cm of the eluate, is recorded continuously.

A fraction of 3.13 liters is initially collected and this is discarded. The following fraction (1.22 liters), which corresponds to an absorbency peak at 230 nm, is introduced into a tube of NOJAX regenerated cellulose and is dialysed for three days at +4° C., against demineralised water (3×40 liters), and the retained material (1,300 cc) is then lyophilised. The solid obtained is taken up in demineralised water (93 cc) and the solution is dialysed, with the same membrane as above, for 48 hours, at +4° C., against demineralised water (2×20 liters). The retained material is lyophilised.

Figure 2:
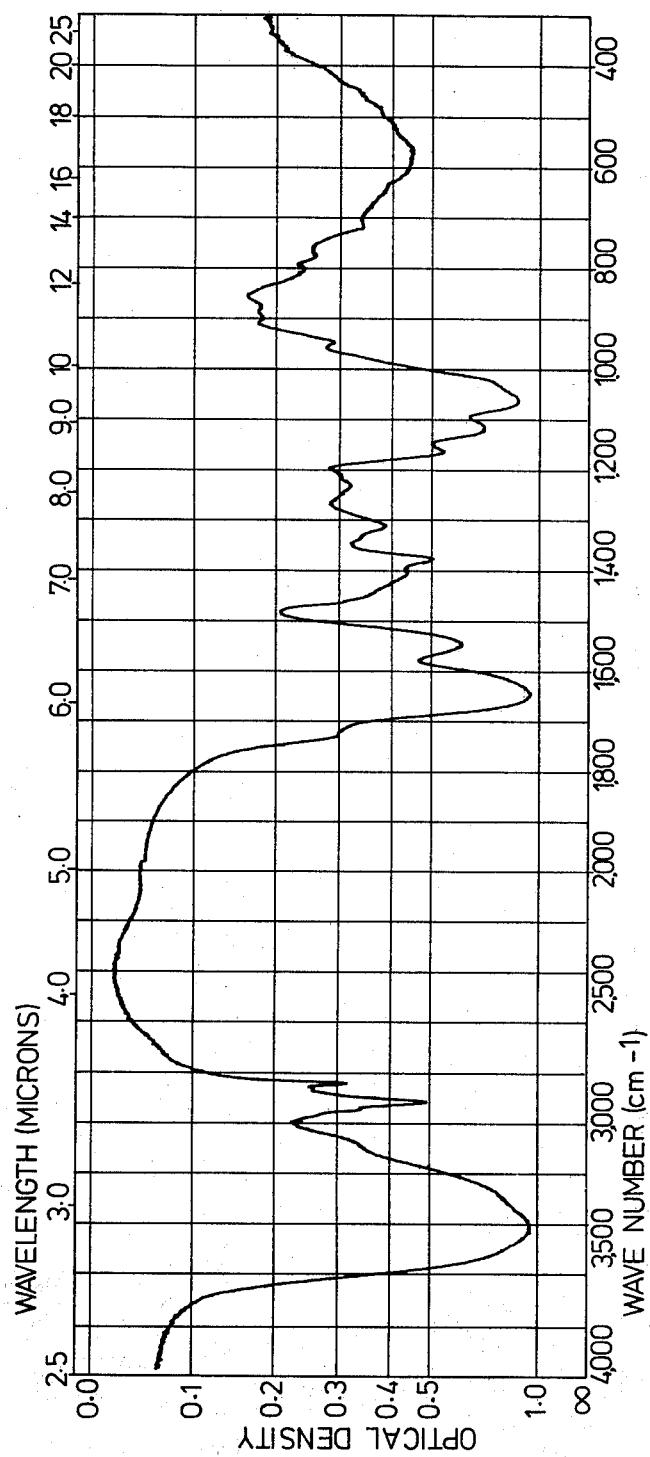

The substance 41,200 RP (1.3 g) is thus obtained and this has the following characteristics:
appearance: white amorphous powder;
UV spectrum: this spectrum is shown in FIG. 1;
infrared spectrum (determined using KBr discs): this spectrum is shown in FIG. 2, in which the wavelength expressed in microns (upper scale), and the wavenumbers in cm$^{-1}$ (lower scale) have been plotted on the abscissae and the percentage transmission has been plotted on the ordinate.

The following Table indicates the main infrared absorption bands of the substance 41,200 RP, expressed in wavenumbers (cm$^{-1}$):

| | | |
|---|---|---|
| 3,420 cm$^{-1}$ vs (including H$_2$O) | 1,440 cm$^{-1}$ sh | 900 cm$^{-1}$ w |
| 3,280 cm$^{-1}$ sh. | 1,405 cm$^{-1}$ sh. | 875 cm$^{-1}$ w |
| 3,090 cm$^{-1}$ sh. | 1,375 cm$^{-1}$ s | 800 cm$^{-1}$ m |
| 2,970 cm$^{-1}$ sh. | 1,335 cm$^{-1}$ sh. | 775 cm$^{-1}$ w |
| 2,950 cm$^{-1}$ sh. | 1,310 cm$^{-1}$ m | 720 cm$^{-1}$ sh. |
| 2,920 cm$^{-1}$ s | 1,230 cm$^{-1}$ m | 630 cm$^{-1}$ sh. |
| 2,845 cm$^{-1}$ m | 1,210 cm$^{-1}$ sh. | 560 cm$^{-1}$ s (including H$_2$O) |
| 2,680 cm$^{-1}$ sh. | 1,160 cm$^{-1}$ s | 520 cm$^{-1}$ sh. |
| 2,100 cm$^{-1}$ vw | 1,115 cm$^{-1}$ s | 480 cm$^{-1}$ sh. |
| 1,730 cm$^{-1}$ sh. | 1,060 cm$^{-1}$ vs | 450 cm$^{-1}$ sh. |
| 1,645 cm$^{-1}$ vs | 1,025 cm$^{-1}$ sh. | 400 cm$^{-1}$ sh. |
| 1,545 cm$^{-1}$ s | 945 cm$^{-1}$ m | 365 cm$^{-1}$ sh. |
| 1,460 cm$^{-1}$ sh. | | | vs = very strong
s = strong
m = medium
w = weak
vw = very weak
sh. = shoulder composition: water (Fischer): 3.8%;
referring to the dry material:
  aminoacids: 12.3% (of which 7% is alanine);
  glucose: 11.95%;
  nucleic acids: less than 1.3% (according to the UV spectrum);
  amino-sugars: 16.3;
elementary analysis: C=45.58%, H=7.47%, N=4.85%, O=37%, P=1.17%, Cl=0.25%, Na=2.36%, Ca=1.33% and S is less than 0.5%;
electrophoresis In a 1% w/v agarose gel, with a barbital buffer at pH 8.6 and under a voltage of 6 V/cm, 41,200 RP migrates towards the anode at a speed of about 11 mm per hour. (The product is detected by Schiff's reagent, after oxidation with periodic acid, or by Sudan black B).

EXAMPLE 2

The procedure of Example 1(A) is followed. After cultivation for 16 hours, the must is cooled to 4° C. and its pH is adjusted to 3 by adding hydrochloric acid. The cells are isolated by centrifugation at 4,000 rpm. The acid cell cake is then heated in an autoclave for 45 minutes at 122° C. After cooling, the cells are washed with ethanol and then dried.

Then, following the procedures of Example 1(B) and 1(C), and using the same amounts, the substance 41,200 RP (0.55 g) is obtained in the form of a white amorphous powder having the following characteristics:
composition: water (Fischer): 6%;
referring to the dry material:
  aminoacids: 17.7% (of which 7.2% is alanine);
  glucose: 10.5%;
  nucleic acids: less than 3%;
  amino-sugars: 15.2%;
elementary analysis: C=46.90%, H=7.32%, N=5.38%, O=35%, P=1.08%, Cl=0.18%, Na=2.26%, Ca=1.83% and S is less than 0.5%.

The infrared spectrum of this product is identical to that of the substance 41,200 RP obtained in Example 1.

The present invention includes within its scope pharmaceutical compositions comprising 41,200 RP or an alkali metal or alkaline earth metal salt thereof, in association with one or more compatible and pharmaceutically acceptable carriers or diluents and, optionally, at least one other therapeutically active product, such as an antibiotic. Preferably, these compositions are administered parenterally or intranasally. The invention includes especially such compositions made up for parenteral or intranasal administration.

Preparations according to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants, in particular wetting, emulsifying and dispersing agents. They may be sterilized by, for example, incorporation in the compositions of sterilizing agents, or by irradiation using $\beta$ rays. They may also be manufactured in the form of sterile solid compositions, which can be dissolved or dispersed in sterile water or some other sterile injectable medium immediately before use.

The compositions for intranasal administration may be in the form of sterile suspensions, emulsions or aqueous solutions, which may optionally be associated with a compatible propellant.

The compositions according to the invention are particularly useful in human or veterinary therapy for the immunological treatment (immunotherapy) of cancer, if appropriate in combination with a suitable anti-cancer chemotherapy or during remissions induced by the latter.

The compositions can also be used for increasing resistance to viral, bacterial, fungal or parasitic infections, for stimulating the natural defences of the organism acting specifically against these infections, for reinforcing, by intranasal administration, the natural barriers against respiratory infections, or for exerting an adjuvant effect on specific immunisation during the concomitant administration of a bacterial, viral or parasitic vaccine.

The compositions of the invention also make it possible to restore the appropriate immunological responses in the case of subjects showing conditions of immunodeficiency which are congenital or result from senescence or from immunosuppressive treatments.

In human therapy, the doses depend on the desired effect and the duration of the treatment; for an adult, they are generally between 0.1 and 10 mg per day, administered parenterally.

The following Example illustrates a composition according to the invention.

EXAMPLE 3

A solution containing the substance 41,200 RP in the form of a salt (5 g; sterilised beforehand by irradiation with $\beta$ rays) in an injectable sterile solution (100 cc) is prepared. This solution is distributed under aseptic conditions, in 5 cc ampoules at a rate of 2 cc per ampoule. The ampoules are sealed. They each contain 100 mg of active ingredient.

We claim:

1. The substance designated 41,200 RP which, when isolated from the cells of *Micrococcus sedogenes* M78 (NRRL B-3505), is an amorphous, white, water-soluble powder, containing carbon, hydrogen, oxygen, nitrogen, phosphorus, sulphur, chlorine, sodium and calcium; its elementary composition (calculated for the dry material) is approximately C=45–47%, H=7.1–7.6%, O=35–38% (by difference), N=4.0–5.7%, P=0.9–1.2%, Cl=0.1–0.4%, S is less than 0.5%, Na=2.0–3.0%, and Ca=0.9–1.9%; it comprises (in the anhydrous state) 11 to 18% of aminoacids (of which 5.5 to 7.5% is alanine), 10 to 17% of glucose, 10 to 17% of amino-sugars and less than 5% of nucleic acids; its infrared spectrum (determined on tablets of a mixture with KBr) shows principal absorption bands as follows: 3,420 (very strong; including water), 3,280 (shoulder), 3,090 (shoulder), 2,970 (shoulder), 2,950 (shoulder) 2,920 (strong), 2,845 (medium), 2,680 (shoulder), 2,100 (very weak), 1,730 (shoulder, 1,645 (very strong), 1,545 (strong), 1,460 (shoulder), 1,440 (shoulder), 1,405 (shoulder), 1,375 (strong), 1,335 (shoulder), 1,310 (medium), 1,230 (medium), 1,210 (shoulder), 1,160 (strong), 1,115 (strong), 1,060 (very strong), 1,025 (shoulder), 945 (medium), 900 (weak), 875 (weak), 800 (medium), 775 (weak), 720 (shoulder), 630 (shoulder), 560 (strong; including water), 520 (shoulder), 480 (shoulder), 450 (shoulder), 400 (shoulder) and 365 (shoulder) cm$^{-1}$; and it possesses immunostimulant properties; and alkali metal and alkaline earth metal salts thereof.

2. A process for the preparation of the substance 41,200 RP, which comprises:
   (a) treating an aqueous suspension of cells of *Micrococcus sedogenes*, M 78 strain (NRRL B-3505), with lysozyme, at a constant pH of from 6.5 to 8, for 1 to 3 hours and at a temperature of from 30° to 40° C.;
   (b) isolating a crude product in the form of a salt, from the liquid phase of the resulting suspension and purifying it by progressive precipitation of impurities from its aqueous solution using calcium chloride in order to obtain a substance designated 32,919 RP which may be in the form of an alkali metal or alkaline earth metal salt thereof; and
   (c) purifying the substance 32,919 RP or salt thereof by treating its aqueous solution with phenol and then fractionating the product on a molecular sieve, collecting the high molecular weight fraction and isolating the substance 41,200 RP from that fraction, optionally followed by the step of converting by known methods the 41,200 RP obtained into an alkali metal or alkaline earth metal salt thereof.

3. A process according to claim 2 in which from 2 to 20 mg of lysozyme are used per gram of dried cells employed.

4. A process according to claim 2 in which the treatment with lysozyme is carried out at a pH of about 7.

5. A process according to claim 2 in which the treatment with lysozyme is carried out for two hours.

6. A process according to claim 2 in which, the cells of *Micrococcus sedogenes* M78 strain (NRRL B-3505), before treatment in an aqueous suspension with lysozyme, are dried and optionally heated at a temperature of from 110° to 130° C., at a pH of from 2 to 4, for 30 to 60 minutes.

7. A process according to claim 2 in which the crude product is dissolved in water at a concentration of from 10 to 40 grams per liter for purification by progressive precipitation of impurities using calcium chloride.

8. A process according to claim 7 in which the concentration is 20 grams per liter.

9. A process according to claim 2 in which the progressive precipitation of impurities is carried out by adding to the aqueous solution of the crude product a concentrated solution of calcium chloride until a final concentration of from 5 to 50 grams per liter is obtained.

10. A process according to claim 9 in which the final concentration is 10 grams per liter.

11. A process according to claim 2 in which the concentration of the aqueous solution of 32, 919 RP is from 10 to 50 grams per liter.

12. A process according to claim 11 in which the concentration is 25 grams per liter.

13. A process according to claim 2 in which the aqueous solution of 32, 919 RP is washed for 15 to 60 minutes at a temperature of about 65° C. with an equal volume of a phenol/water mixture.

14. A process according to claim 13 in which the phenol/water mixture contains 10% (w/w) of water and the washing is carried out for 30 minutes.

15. A process according to claim 2 in which, after the aqueous solution of 32, 919 RP has been treated with phenol, the aqueous phase is separated off and washed with chloroform to remove dissolved phenol.

16. A process according to claim 2 in which, prior to fractionating the product on a molecular sieve, the product is dissolved in water buffered to pH 7 using an alkali metal acetate.

17. A process according to claim 16 in which the alkali metal acetate is sodium acetate.

18. A pharmaceutical composition for the immunological treatment of cancer or for increasing resistance to viral, bacterial, fungal or parasitic infections which comprises 41, 200 RP as defined in claim 1 or an alkali metal or alkaline earth metal salt thereof in association with a significant quantity of one or more compatible and pharmaceutically acceptable carriers or diluents.

19. The substance designated by the number 32, 919 RP which, when isolated from cells of the *Micrococcus sedogenes* M 78 strain (NRRL B-3505) consists of 24 to 33% of aminoacids, 26 to 33% of nucleic acids, 11 to 17.5% of amino-sugars and 2.8 to 4.3% of polysaccharides, and the elementary composition of which is approximately: $C=44-48\%$, $H=5.2-6.7\%$, $O=29-33\%$, $N=10.0-11.6\%$, $P=2.3-3.7\%$, S is less than 0.5%, $Na=3.0-3.8\%$ and $Ca=0.15-0.50\%$, and alkali metal and alkaline earth metal salts thereof which are useful in the preparation of 41, 200 RP.

* * * * *